(12) United States Patent
Galloway (10) Patent No.: US 10,145,850 B2
(45) Date of Patent: Dec. 4, 2018

(54) ASSAY

(76) Inventor: David Brian Galloway, Craibstone (GB)

( * ) Notice: Subject to any disclaimer, the term of this patent is extended or adjusted under 35 U.S.C. 154(b) by 1761 days.

(21) Appl. No.: 13/000,942

(22) PCT Filed: Jun. 18, 2009

(86) PCT No.: PCT/GB2009/001531
§ 371 (c)(1),
(2), (4) Date: Mar. 31, 2011

(87) PCT Pub. No.: WO2009/156711
PCT Pub. Date: Dec. 30, 2009

(65) Prior Publication Data
US 2011/0184073 A1    Jul. 28, 2011

(30) Foreign Application Priority Data

Jun. 24, 2008 (GB) .................... 0811567.7

(51) Int. Cl.
*G01N 33/574* (2006.01)
*G01N 33/53* (2006.01)
*C07K 16/00* (2006.01)

(52) U.S. Cl.
CPC .............. *G01N 33/57434* (2013.01)

(58) Field of Classification Search
CPC ....... G01N 33/574; G01N 33/53; C07K 16/00
USPC ............... 435/7.23, 7.1; 530/388.1
See application file for complete search history.

(56) References Cited

U.S. PATENT DOCUMENTS

| | | | |
|---|---|---|---|
| 6,303,323 B1 * | 10/2001 | Laskey et al. | 435/7.23 |
| 2002/0136715 A1 | 9/2002 | Leveugle | 424/130.1 |
| 2007/0237770 A1 | 10/2007 | Lai | 424/138.1 |

FOREIGN PATENT DOCUMENTS

| | | |
|---|---|---|
| WO | WO 1999/021014 | 4/1999 |
| WO | WO 2006/133560 | 12/2006 |

OTHER PUBLICATIONS

Piaton et al. (BMC Clinical Pathology 2005, 5 (9), p. 1-7).*
Meng et al. (Clin Cancer Res, 2001, 7: 2712-2718).*
Bolduc et al. (CUAJ, 2007, 1 (4): 377-381).*
Oesterling et al. (J. Urol., 1991, 145: 907-923).*
Stoeber, K. et al., "Diagnosis of Genito-Urinary Tract Cancer by Detection of Minichromosome Maintenance 5 Protein in Urine Sediments," *J. of the National Cancer Institute*, vol. 94, No. 14, p. 1071-1079, Jul. 17, 2002.

* cited by examiner

*Primary Examiner* — Yan Xiao
(74) *Attorney, Agent, or Firm* — Gary Baker; Biopatent

(57) ABSTRACT

This invention relates to a method of detecting or determining the presence of prostate cancer cells in a sample of body fluid from a subject comprising: (i) isolating cells from said sample to provide a cell sample; (ii) contacting said cell sample with a specific binding member capable of binding a prostate antigen; and/or (iii) contacting said cell sample with a specific binding member capable of binding a minichromosome maintenance (MCM) polypeptide(s); and (iv) determining the binding of said specific binding member(s) to the cell sample.

12 Claims, 3 Drawing Sheets

ASSAY

CROSS-REFERENCE TO RELATED APPLICATIONS

This application is a US National Phase Application of PCT Patent Application No. PCT/GB2009/001531, filed Jun. 18, 2009, which claims priority to GB Patent Application No. 0811567.7, filed Jun. 24, 2008.

FIELD OF THE INVENTION

This invention relates to a method for the detection of prostate cancer cells in a body fluid such as urine.

BACKGROUND TO THE INVENTION

Previous studies have identified minichromosome maintenance proteins (MCM) as key regulators in the cell cycling process of epithelial tissue (see WO99/21014 and Gonzalez et al; Nature Reviews/Cancer, Vol 5: pp 135-141, February 2005). Multiple conserved mechanisms limit DNA replication to once per cell cycle. An essential role in proliferation for MCMs and their regulators makes them potentially important biomarkers for routine clinical use in cancer detection and prognosis.

MCMs were identified as useful biomarkers of "cell cycle state", i.e. whether a cell is capable of proliferating rather than being quiescent or senescent. Expression of all 6 MCMs (MCM 2-7) is seen throughout all phases of the cell cycle and is down regulated following exit from the cell cycle into quiescence, differentiation or senescence. This is evident on immunohistochemical examination of normal stratified epithelium, covering a number of tissues including cervix, bladder, colon and oropharynx among other epithelial tissues. In each of these cases, MCMs are confined to the basal proliferative compartment and are absent in the terminally differentiated superficial keratinocytes. By contrast, in pre-invasive epithelial lesions, the proliferative compartment progressively expands with increasing histological grade and this is paralleled by the appearance of MCM positive cells at the surface of the epithelium (more than 90% in high grade squamous epithelial lesions in for example the cervix and approximately 40% in low grade squamous intraepithelial lesions in the same tissue).

The ability of MCMs to distinguish cycling cells from quiescent cells prompted a potential clinical application in cancer screening approaches that relies on the detection of malignant or pre-malignant cells exfoliated from surface epithelia such as in cervical screening or indeed in bladder screening using cell detection techniques from the urine of patients affected by Transitional Cell Carcinoma of the bladder.

The present invention concerns a screen for the detection of prostate cancer. Although MCMs can be used as targets in the detection of malignant cells in a body fluid such as urine, they are not tissue specific. There is, therefore, a need for a means of specifically detecting prostate cancer cells in urine. The present invention is based on the determination that prostate epithelial cells can be detected in urine which can in turn be analysed for malignancy.

Thus according to a first aspect of the present invention there is provided a method for detecting or determining the presence of prostate cancer cells in a sample of body fluid from a subject comprising:
(i) isolating cells from said sample to provide a cell sample;
(ii) contacting said cell sample with a specific binding member capable of binding a prostate antigen; and/or
(iii) contacting said cell sample with a specific binding member capable of binding a minichromosome maintenance (MCM) polypeptide(s); and
(iv) determining the binding of said specific binding member(s) to the cell sample.

Typically the body fluid is not blood or cerebrospinal fluid. The body fluid may be urine or semen. Alternatively the body fluid may be faeces. Preferably the body fluid is urine. Preferably the subject is human.

Cells may be isolated from the body fluid sample by any means known to the skilled person. Typically the cells are isolated by either centrifugation or filtration of the body fluid sample. Preferably the cells are isolated by filtration of the body fluid sample. In a preferred method of the invention the sample is subject to antigen retrieval. Antigen retrieval is standard in the art (see Hiraiwa et al refer to Shin et al (1991) Lab. Invest. 64, 693-702 which provides an exemplary approach). Antigen retrieval conditions may include contacting the cell sample with pH7.8 EDTA buffer at 95° for 45 min in water bath or Microwave.

In a method of the invention the prostate antigen may be an antigen specific for prostate tissue. The prostate antigen may be present in normal (i.e. non-cancerous) and in prostate tumour cells. Examples of prostate antigens include, but are not limited to, Prostatic Acid Phosphatase (PSAP), Prostate Specific Antigen (PSA), Prostate Specific G Protein Coupled Receptor (PSGR), and a-Methylacyl-coenzyme-A racemase (AMACR). Preferably the prostate antigen is PSAP or PSGR. In one embodiment of the invention the prostate antigen is PSA.

In a method of the invention the MCM is selected from the group consisting of MCM 2, 3, 4, 5, 6 and 7. The MCM may be a combination of two or more different MCMs, for example, two different MCMs selected from the group consisting of MCM 2, 3, 4, 5, 6 and 7. For example the MCM may include MCM2 and one other MCM selected from MCM 3, 4, 5, 6 and 7. By way of further example the MCM may include MCM5 and one other MCM selected from MCM 2, 3, 4, 6 and 7. In a preferred method of the invention, the MCM is selected from the group consisting of MCM 2, 3, 5 and 7. In a further preferred method of the invention, the MCM is selected from the group consisting of MCM 2, 5 and 7.

In a method of the invention the MCM may include MOM 2 and MCM 5. In a further method of the invention the MCM may include MCM 2 and MCM 7. In a yet further method of the invention the MCM may include MCM 5 and MCM 7.

As used herein, a "specific binding member" is a member of a pair of molecules which have binding specificity for one another. The members of a specific binding pair may be naturally derived or wholly or partially synthetically produced. One member of the pair of molecules has an area on its surface, which may be a protrusion or cavity, which specifically binds to and is therefore complementary to a particular spatial and polar organisation of the other member of the pair of molecules. Thus, the members of the pair have the property of binding specifically to each other.

Examples of types of specific binding pairs are antigen-antibody, biotin-avidin, hormone-hormone receptor, receptor-ligand, enzyme-substrate, DNA-DNA (e.g. oligonucleotide). The present invention is generally concerned with antigen-antibody type reactions, although it also concerns small molecules which bind to the antigen defined herein.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic.

Antibodies which are specific for a target of interest, such as MCM or PSA, PSAP, PSGR or AMACR, may be obtained using techniques which are standard in the art. Methods of producing antibodies include immunising a mammal (e.g. mouse, rat, rabbit) with the protein or a fragment thereof or a cell or virus which expresses the protein or fragment. Antibodies may be obtained from immunised animals using any of a variety of techniques known in the art, and screened, for example using binding of antibody to antigen of interest.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region "Specific" is generally used to refer to the situation in which one member of a specific binding pair will not show any significant binding to molecules other than its specific binding partner(s), e.g., has less than about 30%, preferably 20%, 10%, or 1% cross-reactivity with any other molecule.

The specific binding members of the invention will preferably be, in accordance with the present invention, in "isolated" form. Members will generally be free or substantially free of material with which they are naturally associated such as other polypeptides with which they are found in their natural environment, or the environment in which they are prepared (e.g. cell culture) when such preparation is by recombinant DNA technology practised in vitro or in vivo.

Thus the specific binding member of the invention is preferably an antibody, or fragment thereof. Thus, for example in (ii) the specific binding partner member may be an antibody, or fragment thereof, having an antigen binding domain specific for prostate tissue. For example in (iii) the specific binding member may be an antibody, or fragment thereof, having an antigen binding domain specific for MCM.

The antibody may be a polyclonal antibody, monoclonal antibody, single chain antibody or fragment of any of the foregoing. Preferably the specific binding member is a monoclonal antibody. For example in (ii) the specific binding member may be a monoclonal antibody having an antigen binding domain specific for prostate tissue. Monoclonal antibodies specific to PSA (Dako), PSAP (Sigma), PSGR (Abcam) and AMACR (Dako) are known in the art the details of which are included in Attachment 1. For example in (iii) the specific binding member may be a monoclonal antibody having an antigen binding domain specific for MCM. Monoclonal antibodies specific for MCM are known in the art, for example, anti-MCM2 antibody used in the present study has kindly been provided by the Cancer Cell Unit, Hutchison/MRC Research Centre, Hills Road, Cambridge CB2 0XZ.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a method of the invention, the specific binding members of the invention may be labelled with a detectable label, for example a radiolabel such as I or 99Tc, which may be attached to specific binding members of the invention using conventional chemistry known in the art of antibody imaging. Labels also include enzyme labels such as horseradish peroxidise or alkaline phosphatise. Labels further include chemical moieties such as biotin which may be detected via binding to a specific cognate detectable moiety, e.g. labelled avidin.

The reactivities of a specific binding member such as an antibody on normal and test samples may be determined by any appropriate means. Other labels include fluorochromes, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other labels include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. In the examples described below, alkaline phophatase or horseradish peroxidise have been employed.

In a preferred aspect of the invention the method comprises the steps of:
(i) isolating cells from said sample to provide a cell sample;
(ii) contacting said cell sample with a specific binding member for a prostate antigen; and
(iii) determining the binding of said specific binding member to the cell sample.

In an alternative aspect of the invention the method comprises the steps of:
(i) isolating cells from said sample to provide a cell sample;
(ii) contacting said cell sample with a specific binding member for one or more MCM; and
(iii) determining the binding of said specific binding member to the cell sample.

In a further preferred aspect of the invention the method comprises the steps of:
(i) isolating cells from said sample to provide a cell sample;
(ii) contacting said cell sample with a specific binding member for prostate antigen; and (iii) contacting said cell sample with a specific binding member, or specific binding members, for a minichromosome maintenance (MCM) polypeptide; and
(iv) determining the binding of said specific binding members to the cell sample.

The step of contacting said cell sample with a specific binding member for a prostate antigen may be carried out separately, sequentially or simultaneously with the step of contacting said cell sample with a specific binding member, or specific binding members, for a Minichromosome maintenance (MCM) polypeptide. In one embodiment of the invention the step of contacting said cell sample with a specific binding member for prostate antigen is carried out simultaneously with the step of contacting said cell sample with a specific binding member, or specific binding members, for a minichromosome maintenance (MCM) polypeptide.

Preferably the step of contacting said cell sample with a specific binding member for prostate antigen is carried out separately and sequentially with the step of contacting said cell sample with a specific binding member, or specific binding members, for minichromosome maintenance (MCM) polypeptide. Thus in a preferred aspect of the invention there is provided a method for detecting or determining the presence of prostate cancer cells in a sample of body fluid from a subject comprising:
(i) isolating cells from said sample to provide a cell sample;
(ii) contacting said cell sample with a specific binding member capable of binding a prostate antigen; followed by
(iii) contacting said cell sample with a specific binding member capable of binding a minichromosome maintenance (MCM) polypeptide(s); and
(iv) determining the binding of said specific binding member(s) to the cell sample.

In a further aspect of the invention there is provided a composition comprising a specific binding member a prostate antigen, for example PSA and/or PSAP, and a specific binding member, or specific binding members, for a minichromosome maintenance (MCM) polypeptide, for example MCM2 and/or MCM5 and/or 7.

A further aspect of the invention provides a kit for use in a method according to the invention said kit comprising a composition according to the invention. One or more other reagents may be included, such as labelling molecules as described herein. Other reagents may include any combination of or all of a blocking agent to decrease non-specific staining, a storage buffer for preserving specific binding member activity during storage, staining buffer and/or washing buffer to be used, for example, during antibody staining, a positive control, a negative control and so on. Positive and negative controls may be used to validate the activity and correct usage of reagents employed in accordance with the invention and which may be provided in a kit. The design and use of controls is standard and well within the routine capabilities of those of ordinary skill in the art. The kit may further comprise instructions for performing the method of the invention.

In a further aspect of the invention there is provided a method for the treatment of prostate cancer in a subject the method comprising:
(i) detecting or determining the presence of prostate cancer cells in a sample of body fluid, for example urine, from said subject according to the method of the first aspect of the invention;
(ii) where prostate cancer cells are detected in said sample, administering to said subject a treatment for prostate cancer.

Another aspect of the present invention provides for a method of categorising prostate tissue as (i) normal or (ii) potentially or actually pre-cancerous or cancerous, dysplastic or neoplastic, the method including determining binding to a body fluid sample of a specific binding member specific binding member capable of binding a prostate antigen; and/or a specific binding member capable of binding minichromosome maintenance (MCM) polypeptide(s). The pattern or degree of binding may be compared with that for a known normal sample and/or a known abnormal sample.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention will now be described by way of example only with reference to the following figures.

EXAMPLES

Materials

| Antigen | Clone | Cat. No. | Supplier |
|---|---|---|---|
| MCM2 | 6A8 | MCA3251Z | AbD Serotec |
| " | D1.9H5 | MCA1859 | AbD Serotec |
| " | 4B8 | M069-3 | MBL International |
| " | SPM196 | Ma1-38102 | Fisher Scientific |
| PSA epitope 3 | PS2 | ab10189 | Abcam |
| PSA epitope 1 | 8A6 | ab10187 | Abcam |
| PSA epitope 4 | 5G6 | ab10186 | Abcam |
| PSA | Rb polyclonal | ab9537 | Abcam |
| PSAP | Rb polyclonal | GTX72749 | GeneTex |
| PSGR | Rb Polyclonal | GTX71863 | GeneTex |

| Antigen | Clone | Supplier | product code |
|---------|-------|----------|--------------|
| MCM3 | JCC07 | Leica Microsystems (Novacastra) | Protein 3NCL-MCM3 |
| MCM5 | CRCT5.1 | Leica Microsystems (Novacastra) | Protein 5NCL-MCM5 |
| MCM7 | DCS-141.1 | Leica Microsystems (Novacastra) | Protein 7NCL-MCM7 |

Example 1

MCM Assay on Urine Collected from Patients with Prostate Cancer

The urines collected from patients with prostate cancer were then transferred to the laboratory where a routine approach to the preparation of liquid based cytology slides was undertaken. In particular, the whole volume urine sample was divided between Falcon tubes for centrifugation and following a standard procedure, the preparation of a cell pellet containing prostate specific epithelial cells was prepared. Comparative PAP stained slides for routine assessment were referred to the Consultant in charge of the Cytopathology Laboratory while slides for immunocytochemistry staining were stored at 4° C. for batch staining and processing thereafter. The documentation relating to Cytoimmunopathology Laboratory staining is described below. In particular, the use of antigen retrieval and EDTA at pH 7.8 at 95° C. for 45 minutes in a water bath was found to be an important component of the pre-stained protocol for cytology slides.

Materials and Methods

Double Staining Protocol for Prostate MCM

This protocol uses the DAKO EnVision™ G|2 Doublestain System (K5361) and is intended for use in immunohistochemistry with either primary mouse and rabbit antibodies for the detection of antigens in formalin-fixed, paraffin embedded tissues or fixed cell smears. This visualization system is designed for the simultaneous detection of two different antigens within one specimen. The system may be used in manual procedures or with Dako Autostainer instruments.

The procedure is a sequential double staining where the first antigen is visualized using HRP/DAB+ and the second antigen is visualized using AP/Permanent Red. Dual Endogenous Enzyme Block inhibits endogenous alkaline phosphatase, peroxidase, and pseudoperoxidase activity present in some tissues. After blocking of endogenous enzymes, the first step is incubation of the specimen with an optimally diluted primary mouse or rabbit antibody, followed by incubation with the Polymer/HRP reagent. This reagent is an HRP-conjugated dextran polymer that also carries antibodies to mouse and rabbit immunoglobulins. The reaction is visualized by DAB+ Chromogen. Following a blocking step using the Doublestain Block reagent, the specimen is incubated with a second optimally diluted primary mouse or rabbit antibody. In the next step Rabbit/Mouse (LINK) is added; a dextran polymer carrying antibodies to mouse and rabbit immunoglobulins, followed by incubation with the Polymer/AP reagent. Permanent Red Chromogen visualizes the second reaction. All specified reagents, except the primary antibodies, are provided with the kit.

Autostainer Staining Protocol 1$^{st}$ Antibody (MCM-2), supplied by the Cancer Cell Unit, MRC, Cambridge at 1:40 dilution. Autostainer Staining Protocol 2$^{nd}$ Antibody (MCM-2) supplied by the Cancer Cell Unit, MRC, Cambridge at 1:40 dilution.

A   Prestain Protocol Histology Slides
1. Slides rehydrate from Xylene > alcohol; spirit; water
2. Antigen retrieval for 10 + 10 mins in pH 6 citrate buffer in a microwave
3. Washed water then load on to Autostainer B   Prestain Protocol cytology slides
1. Slides immersed in 50% ethanol for 5 mins
2. Rinsed in distilled water then placed in TBS
3. Antigen retrieval pH 7.8 EDTA buffer at 95° for 45 min in water bath (or Tissue grade Microwave)
4. Allowed to cool at room temp for 20 mins
5. Rinsed in water then buffer before being placed on Autostainer C1   Autostainer Staining Protocol 1$^{st}$ Antibody (MCM-2) (envision HRP) DAKO G/2 Double stain kit (K5631)
1. Dual Endogenous Enzyme Block for 5 mins
2. Rinsed × 2 with TBS buffer
3. Antibodies and controls added for 60 mins
4. Rinsed × 2 TBS buffer
5. Envision Polymer HRP added for 30 mins
6. Rinsed × 2 TBS buffer
7. DAB substrate for 5 mins ⇓ (Note: The programme follows on to second arm as indicate in step 8 onwards. However it should be noted that we have found considerable clearer definition of staining by removing slides from
Autostainer and placing them back in retrieval buffer for 5 minutes
in the microwave before loading them back on to the Autostainer.
If the microwave step is used the "Alkaline phosphate (second Arm) is run as a separate programme at this point on the Autostainer.

C2   Autostainer Staining Protocol 2$^{nd}$ Antibody (MCM-2) (envision Alkaline Phosphatase) DAKO G/2 Double stain kit (K5631)
8. Double-stain Block 3 mins (Auxiliary reagent)
9. Rinsed × 2 with TBS buffer
10. 2$^{nd}$ set of primary Antibodies and controls added for 60 mins
11. Rinsed × 2 with TBS buffer
12. G/2 Rabbit/mouse link 15 mins (secondary reagent)
13. Rinsed × 2 with TBS buffer
14. Envision Polymer Alk Phos added for 15 mins (tertiary reagent)
15. Rinsed × 2 with TBS buffer
16. Liquid (permanent) red Alk Phos Substrate 7 mins (see notes******)
17. Rinse water
Post Stain Protocol D
1. Rinsed in water
2. CuSo4 for 5 mins
3. Rinse in water
4. Counterstain: Haematoxylin 10 secs
5. Rinse water
6. Scott's tap water 40 secs
7. Rinse water
8. Allow slides to air dry
9. Coverslip with either non-aqueous mount or permanent mount (see notes)

Alkaline Phos Substrate

Alkaline phosphatase (Liquid permanent red) this reagent must be made up and put into to the autostainer no more than 30 minutes before it is needed.

After counterstaining slides should not be de-hydrated through Alcohol and Xylene—slides should simply be air dried then mounted with either aqueous Mounting medium (we use DAKO Faramount Aqueous mounting medium S3025) or if you use permanent mount again simply air dry slides then use Dako permanent mount S3026 or equivalent. Note that liquid red can be red under both normal light, or fluorescent light using a "Texas red/Rhodamine" filter—and this can be useful in discriminating between the DAB and the Alkaline phosphatase staining.

Results 38 samples from patients with known prostate cancer have been collected in an outpatient Prostate Cancer Clinic. To date, 22 out of the 38 samples have been processed. 22 out of the 22 slides tested confirmed the presence of prostate cancer in varying grades (grades 1-4) and all have shown MCM positive cells, i.e. clear evidence of malignancy at varying grades of invasiveness.

Example 2

Materials and Methods
Protocol for Single Staining of Prostate Cells in LBC Urine Preparations (Bladder Cell Control)

CytoimmunoPathology Laboratory Staining protocol for prostate PSA Stud

A Prestain Protocol Histology Slides
 1. Slides rehydrate from Xylene > alcohol; spirit; water
 2. Antigen retrieval for 10 + 10 mins in pH 6 citrate buffer in a microwave
 3. Washed water then load on to Autostainer
B Prestain Protocol cytology slides
 1. Slides immersed in 50% ethanol for 5 mins
 2. Rinsed in distilled water then placed in TBS
 3. Antigen retrieval in citrate buffer (pH 6.8) 20 minutes in a standard microwave oven.
 4. Allowed to cool at room temp for 20 mins
 5. Rinsed in water then buffer before being placed on Autostainer
C Autostainer Staining Protocol (envision HRP) Dako kit 5007
 1. Peroxidase block with $H_2O_2$ for 5 mins
 2. Rinsed × 3 with TBS buffer
 3. Antibody PSA at 1:30,000 dilution and controls added for 60 mins
 4. Rinsed × 2 TBS buffer
 5. Envision HRP added for 30 mins
 6. Rinsed × 2 TBS buffer
 7. DAB substrate for 5 mins
 8. Rinsed
 9. Counterstain:
 10. Rinse in water
 11. CuSO4 for 3 mins
 12. Rinse water
 13. Haematoxylin 10 secs
 14. Rinse water
 15. Scott's tap water 40 secs
 16. Rinsed water
 17. Dehydrated through Spirit × 2; Alcohol and Xylene
 18. Coverslipped with DPX Standard Envision stain used.

Example 3

Figure 1:
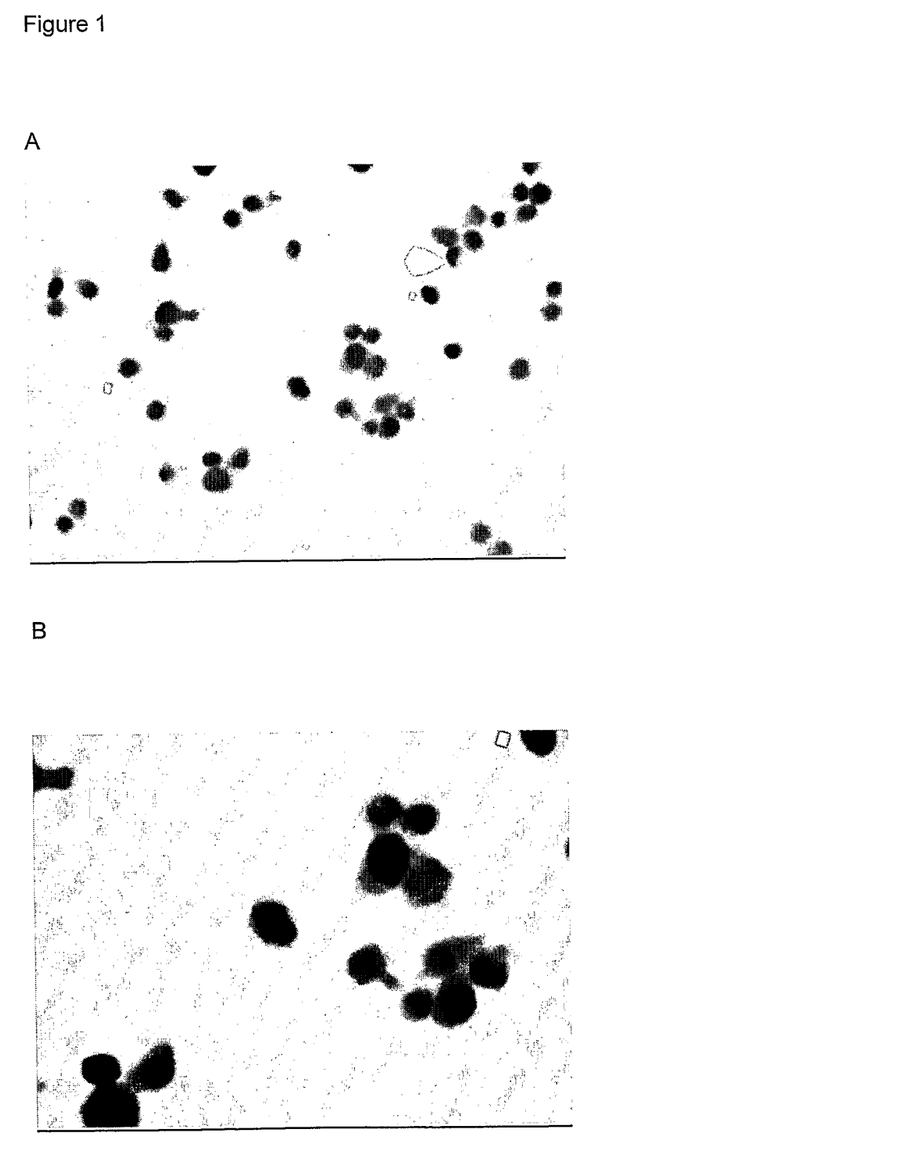
FIG. 1: Photograph of prostate cancer cells (cell line C4-2b) labelled with antibodies MCM-2 and PSA; a) prostate cancer cells showing dark nuclear staining of MCM-2 with a red cytoplasmic stain of PSA; and b) High powered resolution prostate cells showing very dark nuclear staining for MCM2 and the red hue of cytoplasm indicates the presence of PSA.
Figure 2:
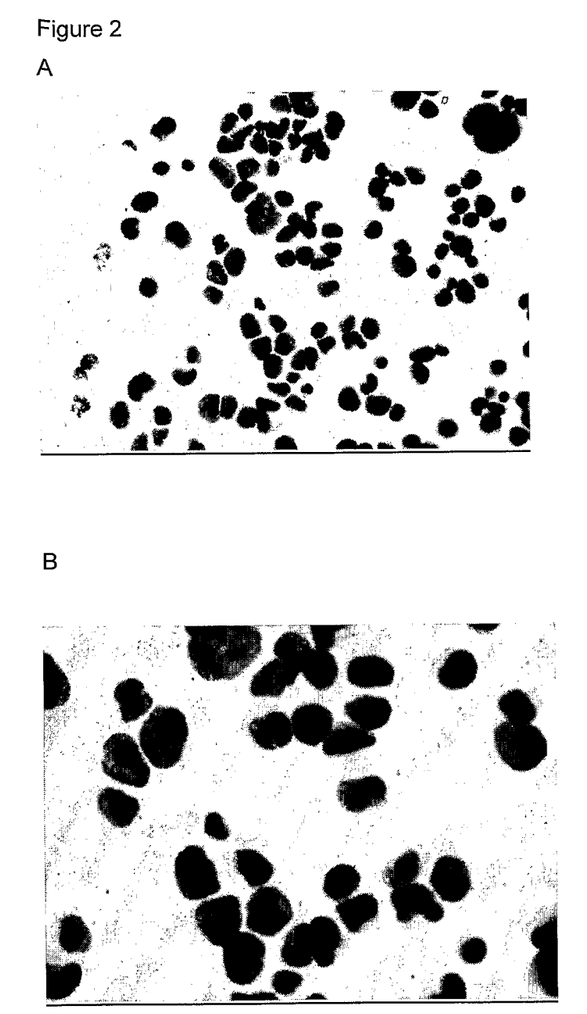
FIG. 2: Photograph of bladder cancer cells (cell line EJ28) labelled with antibodies to MCM-2 and PSA; a) bladder cancer cells showing the target nuclear staining for MCM; no PSA detected; b) High magnification bladder cancer cells showing target nuclear staining cells, no PSA detected.
Figure 3:
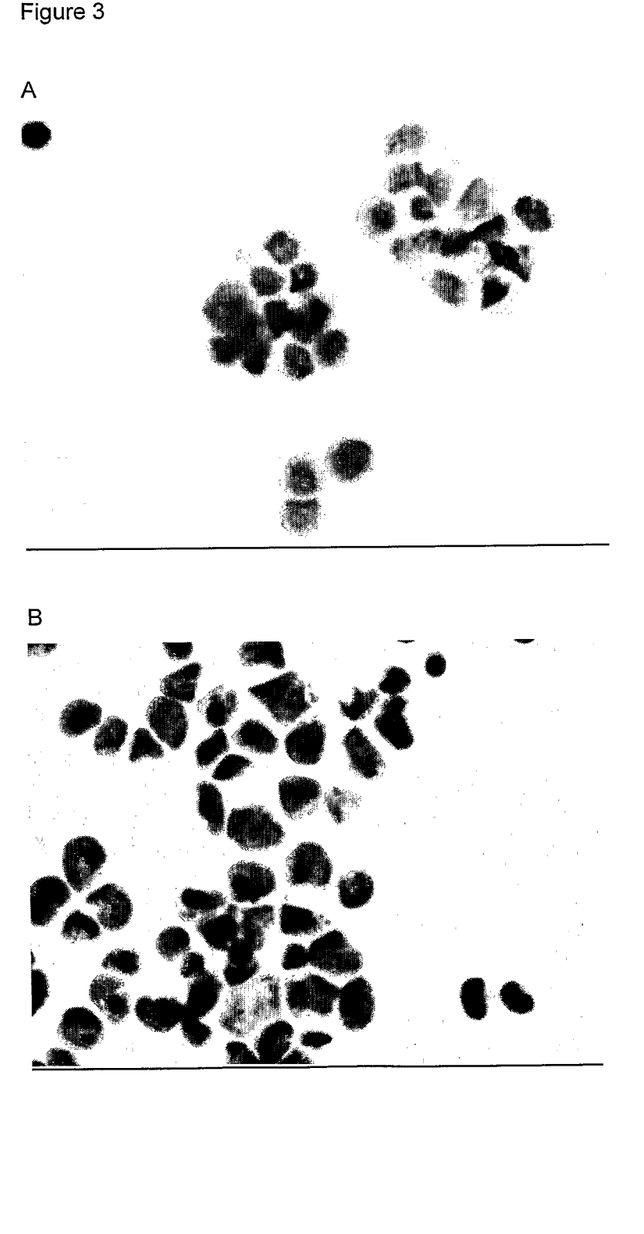
FIG. 3: Photograph of high magnification a) prostate cancer cells (cell line C4-2b) labelled with antibodies to MCM-2 and PSA—showing deep stained nucleus positive for MCM and surrounding red staining cytoplasmic material indicative of PSA; b) bladder cancer cell (cell line EJ-28) s labelled with antibodies to MCM-2 and PSA—showing deep staining nucleic indicative of MCM but total absence of cytoplasmic staining indicative of absence of PSA.

Materials and Methods
MCM and PSA Double Assay on Urine Collected from Patients with Prostate Cancer MCM2 supplied by Cancer Cell Unit, Hutchison/MRC Research Centre, Hills Road, Cambridge CB2 0XZ. PSA antibodies supplied as per attachment at 1:30,000 dilution.
Double-Staining Protocol for Prostate MCM-2/PSA Study
A Prestain Protocol Histology Slides
1. Slides rehydrate from Xylene>alcohol; spirit; water
2. Antigen retrieval for 10+10 mins in pH6 citrate buffer in a microwave
3. Washed water then load on to Autostainer
B Prestain Protocol cytology slides
1. Slides immersed in 50% ethanol for 5 mins
2. Rinsed in distilled water then placed in TBS
3. Antigen retrieval pH7.8 EDTA buffer at 95° for 45 min in water bath (or Tissue grade Microwave)
4. Allowed to cool at room temp for 20 mins
5. Rinsed in water then buffer before being placed on Autostainer
C1 Autostainer Staining Protocol 1st Antibody (MCM-2 at 1:40 dilution) (envision HRP) DAKO G/2 Double stain kit (K5631)
1. Dual Endogenous Enzyme Block for 5 mins
2. Rinsed ×2 with TBS buffer
3. Antibodies and controls added for 60 mins
4. Rinsed ×2 TBS buffer
5. Envision Polymer HRP added for 30 mins
6. Rinsed ×2 TBS buffer
7. DAB substrate for 5 mins
C2. Blocking of 1st reaction:
8. Slides removed from Autostainer washed in Water for three minutes
9. Slides microwaved for 5 minutes in Citrate Buffer pH6
10. Washed tap water for 3 minutes then loaded back on to Autostainer
C3 Auto-stainer Staining Protocol 2nd Antibody (PSA at 1:30,000 dilution) (envision Alkaline Phosphatase) DAKO G/2 Double stain kit (K5631
11. Double-stain Block 3 mins (Auxiliary reagent)
12. Rinsed ×2 with TBS buffer
13. 2nd set of primary Antibodies and controls added for 60 mins
14. Rinsed ×2 with TBS buffer
15. G/2 Rabbit/mouse link 15 mins (secondary reagent)
16. Rinsed ×2 with TBS buffer
17. Envision Polymer Alk Phos added for 15 mins (tertiary reagent)
18. Rinsed ×2 with TBS buffer
19. Liquid (permanent) red Alk Phos Substrate 5 mins
Post Stain Protocol
D 1. Rinsed in water
2. CuSo4 for 5 mins
3. Rinse in water
4. Counterstain: Haematoxylin 10 secs
5. Rinse water
6. Scott's tap water 40 secs
7. Rinse water
8. Allow slides to air dry
9. Coverslip with either non-aqueous mount or permanent mount
Results Reasonable results were obtained with prostate cancer cell lines. The nucleus stained brown (MCM-2) and the cytoplasm stained red (PSA)—see FIGS. 1 to 3. A control bladder cell line stained positive for MCM-2 but negative for PSA. However, clinical samples were only weakly positive (40 tested) for PSA.

Example 4

Reversed MCM-2 and PSA Double Assay on Urine Collected from Patients with Prostate Cancer Given the results obtained in Example 3, we investigated whether weak PSA staining was due to the PSA antigen being destroyed by the heat retrieval process used to recover the MCM-2 antigen. A single peroxidise (brown) stain was carried out using anti-PSA antibody on clinical samples but with no heat retrieval. The results obtained (data not shown) showed a strong staining of clinical samples with the anti-PSA antibody. These results confirmed the presence of prostate cells in LBC urine samples. We then tested whether double staining could be undertaken by staining for PSA first then, after heat retrieval, anti-MCM2 by alkaline phosphatase.
Materials and Methods
PSA and MCM-2 Double Staining Protocol for Prostate Cancer Cells (Bladder Cancer Cells as Control)
A Prestain Protocol Histology Slides
1. Slides rehydrate from Xylene>alcohol; spirit; water
2. Antigen retrieval for 10+10 mins in pH6 citrate buffer in a microwave
3. Washed water then load on to Autostainer B Prestain Protocol cytology slides
1. Slides immersed in 50% ethanol for 5 mins
2. Rinsed in distilled water then placed in TBS (note no heat retrieval)
3. Rinsed in water then buffer before being placed on Autostainer
C1 Autostainer Staining Protocol DAKO G/2 Double stain kit (K5631)
1st Antibody Prostate-Specific Antigen (PSA) Dako Rabbit Polyclonal (A0562) 1:25,000 (envision HRP);
2nd Antibody MCM-2 at 1:40 dilution (envision Alkaline Phosphatase)
1. Dual Endogenous Enzyme Block for 5 mins
2. Rinsed ×2 with TBS buffer
3. Antibodies and controls added for 30 mins
4. Rinsed ×2 TBS buffer
5. Envision Polymer HRP added for 30 mins
6. Rinsed ×2 TBS buffer
7. DAB substrate for 5 mins
8. Slides removed from Autostainer and rinse in Tap water 3 mins
9. Slides placed in EDTA heat retrieval buffer pH7.8 and micro-waved for 20 mins (10+10 mins)
10. Allow to cool for 5 mins before rinsing in tap water 5 mins
11. Slides placed back in to Auto-stainer
12. Double-stain Block 3 mins (Auxiliary reagent)
13. Rinsed ×2 with TBS buffer
14. 2nd set of primary Antibodies and controls added for 60 mins
15. Rinsed ×2 with TBS buffer
16. G/2 Rabbit/mouse link 15 mins (secondary reagent)
17. Rinsed ×2 with TBS buffer
18. Envision Polymer Alk Phos added for 15 mins (tertiary reagent)
19. Rinsed ×2 with TBS buffer
20. Liquid (permanent) red Alk Phos Substrate 7 mins
Note:—this reagent is made up and placed into the autostainer 30 minutes before required as indicated in Double stain kit—We add Levamisole (Dako X3021) at I drop per ml of Substrate solution. Remember to add levamisole
17. Rinse water
Post treatment/Double-staining protocol
Under normal light microscope MCM-2 positive cells will have a red nucleus if these also express PSA this will appear as a strong brown colour in the cytoplasm.
Additional Notes:
Programming of the Autostainer Instrument
Prior to the first application of EnVision™ G|2 Doublestain System on Dako Autostainer Instrument, a new template has to be made. Template: K5361:—* Note we use 2 rinse buffer steps
Alkaline Phosphatase Substrate/
Post Stain Protocol
1. Rinsed in water
2. CuSo4 for 5 mins
3. Rinse in water
4. Counterstain: Haematoxylin 10 secs
5. Rinse water
6. Scott's tap water 30 secs
7. Rinse water
8. Allow slides to dry in slide heater
9. Coverslip with Faramount aqueous mounting medium DAKO
Double-Staining Protocol
Alkaline Phosphatase Substrate
Alkaline phosphatase (Liquid permanent red) this reagent must be made up and put into to the autostainer no more than 30 minutes before it is needed (Batch-Substrate reagent). After counterstaining slides should not be de-hydrated through Alcohol and Xylene—slides should simply be air dried then mounted with either aqueous Mounting medium (we use DAKO Faramount Aqueous mounting medium S3025) or if you use permanent mount again simply air dry or place slides into a Slide (section) dryer i.e. LAMB Heater set at 60° C.) then use Dako permanent mount S3026 or equivalent. If you are using an automated "coverslipper"—slides may be put into xylene without significant loss of stain. Note that liquid red can be red under both normal light, or fluorescent light using a "Texas red/Rhodamine" filter—and this can be useful in discriminating between the DAB and the Alkaline phosphatase staining.
Results
The results obtained (not shown) by reversing the double staining i.e. anti-PSA stain followed by anti-MCM 2 were a significant improvement.
Repeated experiments in the lab indicated that the best outcome for dual staining required PSA staining initially at 1:25,000 followed by the MOM stain at 1:40 dilution. This approach has been adopted throughout the subsequent analysis and throughout the testing of numerous different prostate cells lines.

Example 5

Prostate Marker and MCM Double Assay on Urine Collected from Patients with Prostate Cancer
Experiments are conducted as follows:
Anti prostate antigen antibody staining (PSAP, PSA and PSGR) followed by anti-MCM antibody staining (MCM 2, 3, 5 and 7 alone and in combination).

The invention claimed is:
1. A method of detecting or determining the presence of prostate cancer cells in a sample of body fluid from a subject,
 (i) isolating cells from said sample to provide a cell sample;
 (ii) contacting said cell sample first with a monoclonal antibody or fragment thereof, having an antigen binding domain specific for a prostate antigen;
 (iii) washing said cell sample;
 (iv) contacting said cell sample from step (iii) with a monoclonal antibody or fragment thereof, having an antigen binding domain specific for a minichromosome maintenance MCM-2 polypeptide; and
 (v) determining the binding of both of said monoclonal antibodies or fragments thereof, to the cell sample to detect prostate cancer cells in said subject.
2. The method as claimed in claim 1 wherein the body fluid is urine.
3. The method as claimed in claim 1 wherein the cells are isolated from urine by filtration of urine.
4. The method as claimed in claim 1 wherein the cell sample isolated in (i) is subjected to antigen retrieval.
5. The method as claimed in claim 1 wherein the prostate antigen is an antigen specific for prostate tissue.
6. The method as claimed in claim 1 wherein the prostate antigen is expressed in normal prostate cells.
7. The method as claimed in claim 1 wherein the prostate antigen is expressed in prostate tumor cells.
8. The method as claimed in claim 1 wherein the prostate antigen is selected from the group consisting of Prostatic Acid Phosphatase (PSAP), Prostate Specific Antigen (PSA), Prostate Specific G Protein Coupled Receptor (PSGR) and a-methylacyl-coenzyme-A racemase (AMACR).
9. The method as claimed in claim 1 wherein the monoclonal antibody or fragment thereof is/are labeled with a detectable label.

10. The method as claimed in claim 1 wherein the step of contacting said cell sample with a monoclonal antibody or fragment thereof, having an antigen binding domain specific for a prostate antigen may be carried out separately, sequentially or simultaneously with the step of contacting said cell sample with monoclonal antibody or fragment thereof, having an antigen binding domain specific for a MCM-2 polypeptide.

11. The method as claimed in claim 10 wherein the step of contacting said cell sample with a monoclonal antibody or fragment thereof, having an antigen binding domain specific for prostate antigen is carried out simultaneously with the step of contacting said cell sample with a monoclonal antibody or fragment thereof, having an antigen binding domain specific for a MCM-2 polypeptide.

12. The method of claim 1, wherein the antigen binding domain specific for prostate antigen (PSA) is at 1:25,000 dilution and antibody MCM-2 at 1:40 dilution.

\* \* \* \* \*